Nov. 19, 1963 H. B. LEWIS ETAL Plant Pat. 2,310
AZALEA PLANT
Filed Sept. 28, 1962 2 Sheets-Sheet 1
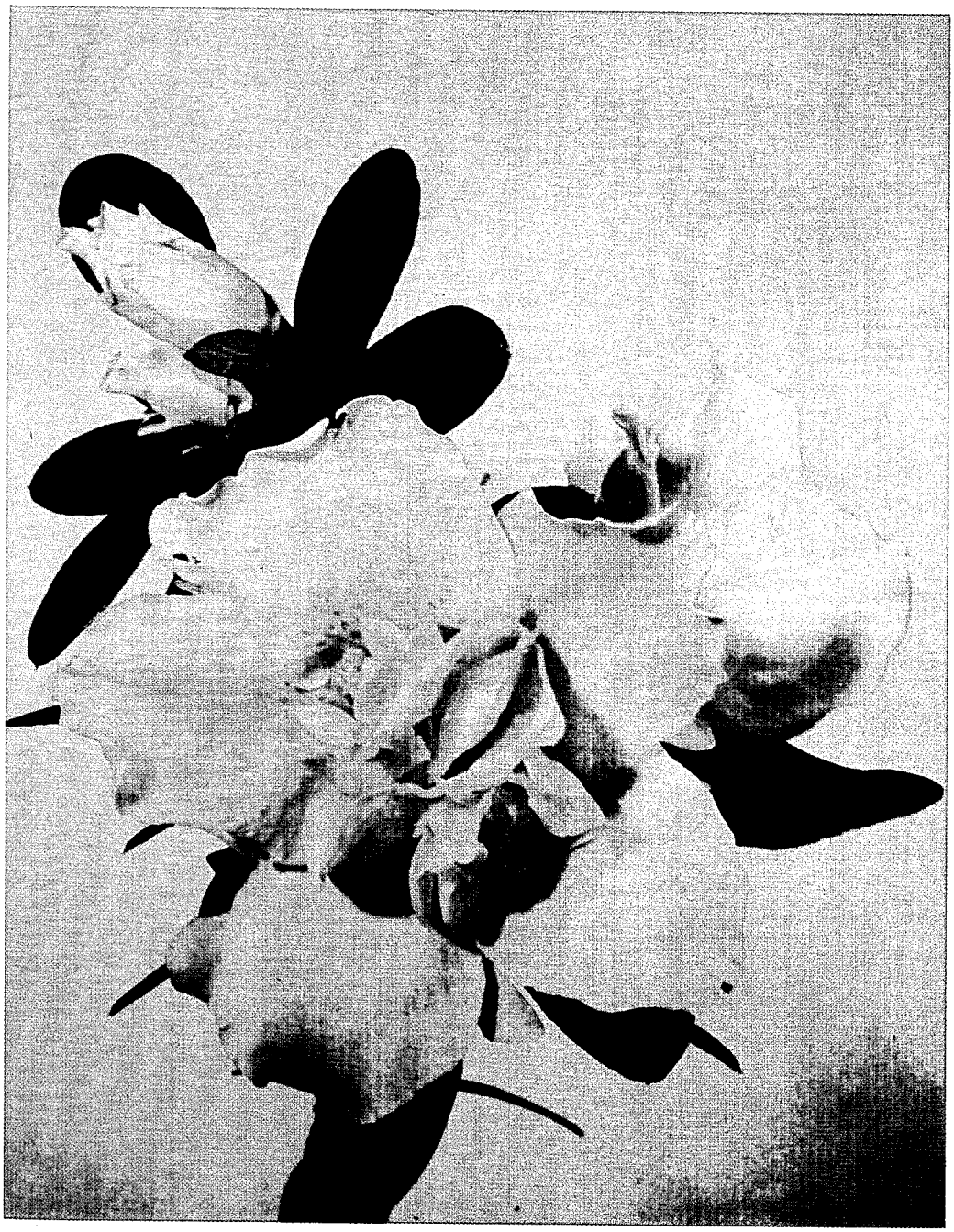
Inventors.
H. B. Lewis and
H. H. Lewis
By: Robbins & Cobb
Attorneys.

Nov. 19, 1963 H. B. LEWIS ETAL Plant Pat. 2,310
AZALEA PLANT
Filed Sept. 28, 1962 2 Sheets-Sheet 2
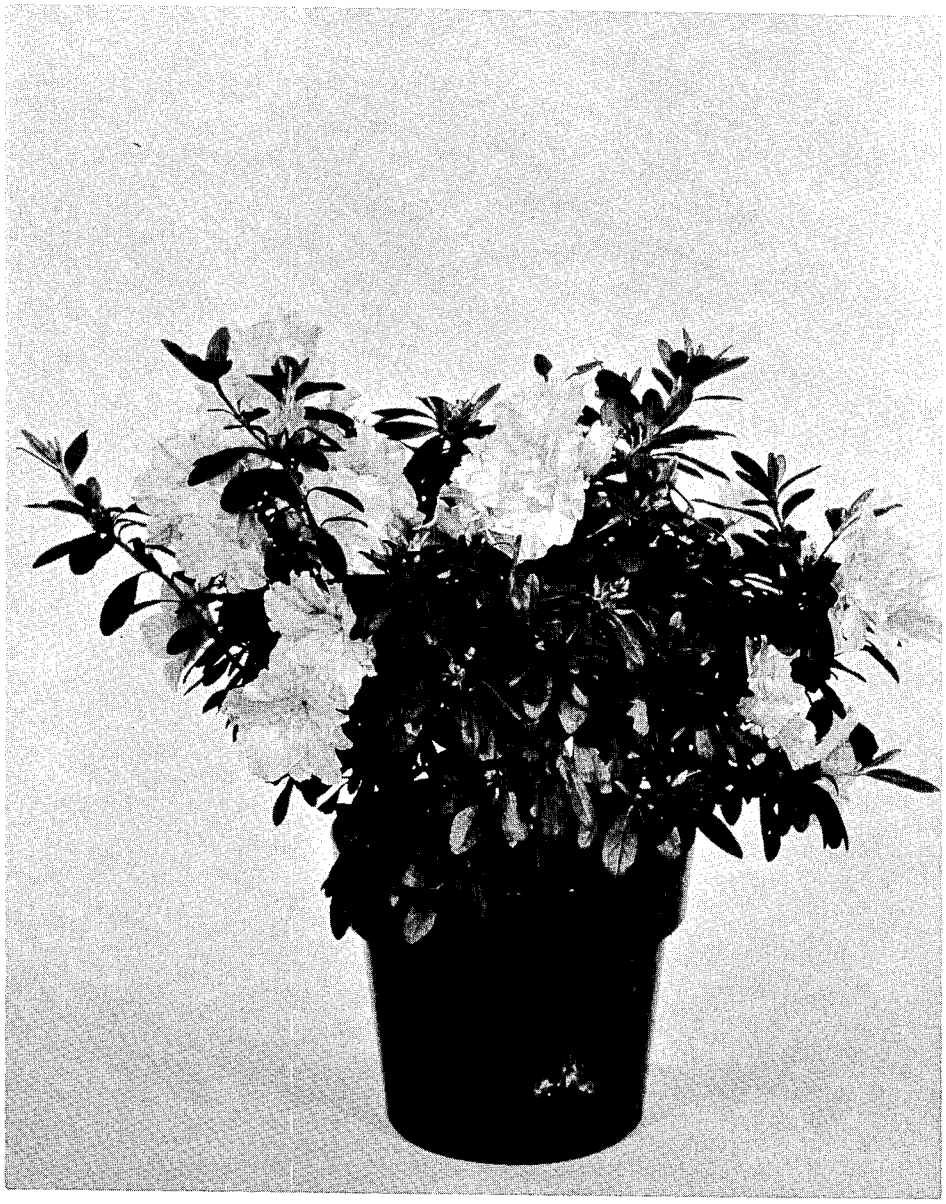
Inventors.
H. B. Lewis and
H. H. Lewis
By: Robb & Robb
attorneys.

United States Patent Office

Plant Pat. 2,310
Patented Nov. 19, 1963

2,310
AZALEA PLANT

Hubert B. Lewis and Helen H. Lewis, both of 16562 E. Leffingwell Road, Whittier, Calif.

Filed Sept. 28, 1962, Ser. No. 227,098
1 Claim. (Cl. Plt.—56)

The present invention delates to a new and distinct variety of azalea plant, which was originated by us by crossing the Belgian Indian Variety known as "Sweet Sixteen" (unpatented) with the variety known as "Mme. Pericat" (unpatented), the former being the seed parent and the latter being the pollen parent.

As the result of this breeding, we have produced a new azalea variety which is endowed with a new and improved combination of characteristics, as evidenced by the following features which are outstanding therein and which distinguish the new variety from its parents, as well as from all other varieties of which we are aware:

(1) Strong, vigorous and fast-growing habits of growth;
(2) A heavy branching habit, with consequent production of a heavy head of flowers;
(3) A semi-double flower form;
(4) A ruffled appearance of the flower buds before opening;
(5) A distinctive, attractive and unusual soft clear pink general color tonality of the flowers, with occasional stripes of darker pink color on some petals;
(6) Good keeping qualities of the flowers; and
(7) A habit of being suitable for forcing.

Our new variety resembles neither parent, except with respect to the shape of the flowers which is somewhat the same as the flower shape of the seed parent, "Sweet Sixteen." The flowers of the new variety are more ruffled and have a much clearer pink color. In its habit of growth, the new variety is vigorous, and fast growing, while the parent variety "Sweet Sixteen" has a dwarf and bushy habit of growth. There is no resemblance of the new variety to the pollen parent, "Mme. Pericat," from the standpoint of leaf or flower, but the new variety has inherited the vigorous growth habit of this parent. The flower color of the new variety is a new and long-desired color in the azalea world.

Asexual reproduction of our new variety by cuttings, as performed at Rivera, California, and at Whittier, California, shows that the foregoing characteristics and distinctions come true to form and are established and transmitted through succeeding propagations.

The accompanying drawings show a typical specimen plant of our new azalea variety as depicted in black and white to illustrate its general form and habit of growth, as well as typical specimens of the flowers and foliage as depicted in color on a somewhat enlarged scale to better illustrate the details thereof.

Th following is a detailed description of our new azalea variety, with color terminology in accordance with the Wilson Horticultural Color Chart, except where general color terms of ordinary dictionary significance are obvious:

Locality where grown and observed: Whittier, California.
Propagation: Holds its distinguishing characteristics through succeeding propagations by cuttings.

*Plant*

Form: Bush.
Habit: Medium size, vigorous growth.
Rooting habit: Easy.
Foliage:
*Size.*—Medium.
*Quantity.*—Normal.
*Color.*—New foliage: upper side—Scheeles Green, Plate 860; under side—Scheeles Green, Plate 860/1. Old foliage: upper side—Spinach Green, Plate 0960/1; under side—Scheeles Green, Plate 860/1.
*Shape.*—Elongated oval.
*Texture.*—Upper side—smooth. Under side—fairly smooth.
*Margin.*—Smooth.
*Aspect.*—Smooth.
*Disease resistance.*—Fair resistance to ordinary diseases to which azalea plants are normally subject, as determined by comparison with other varieties grown under the same cultural conditions at Whittier, California.

*Flowers*

Borne: 2 or 3 to stem; on short and strong stems.
Blooming habit: Free.
Blooming season: Heavy in spring; very suitable for forcing.
Quantity of bloom: Free.
Continuity: Heavy in spring and intermittent thereafter. Lasting quality—long, with little fading.
Petalage: Normally 5 petals to each hose, with tufted center.
*Color.*—Fuchsine Pink, Plate 627/3.
*Texture.*—Medium.
*Appearance.*—Inside—double raised center. Outside—petals slightly ruffled.
*Shape.*—Semi-double hose in hose.
*Arrangement.*—Inner hose is offset from outer hose and has raised tufted center.
Bud: Rather ruffled before opening. Color—Fuchsine Pink, Plate 627/2.

*Reproductive Organs*

Stamens: From 5 to 7 in number; some attached to center petals. Color—pink.
Pollen: Sparse. Color—white.
Styles: Color—pink.
Ovaries: Normal.

We claim:

A new and distinct variety of azalea plant, substantially as herein shown and described, characterized particularly as to novelty by the unique combination of strong, vigorous and fast-growing habits of growth, a heavy branching habit, with consequent production of a heavy head of flowers, a semi-double flower form, a ruffled appearance of the flower buds before opening, a distinctive, attractive and unusual soft clear pink general color tonality of the flowers, with occasional stripes of darker pink color on some of the flower petals, good keeping qualities of the flowers, and a habit of being suitable for forcing.

No references cited.